US00PP18675P2

(12) United States Plant Patent
Miedema-Jorna

(10) Patent No.: US PP18,675 P2
(45) Date of Patent: Apr. 1, 2008

(54) **NEW GUINEA *IMPATIENS* PLANT NAMED 'TAMAR WHITE IMPROVED'**

(50) Latin Name: *Impatiens hawkeri*
Varietal Denomination: Tamar White Improved

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 11/637,858

(22) Filed: Dec. 12, 2006

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
(74) *Attorney, Agent, or Firm*—C. A. Whealy

(57) ABSTRACT

A new and distinct cultivar of *Impatiens* plant named 'Tamar White Improved', characterized by its upright and outwardly spreading growth habit; mounded plant form; freely branching habit; dark green-colored leaves; freely flowering habit; large white-colored flowers; and good garden performance.

2 Drawing Sheets

Botanical designation: *Impatiens hawkeri.*
Cultivar denomination: 'Tamar White Improved'.

BACKGROUND OF THE INVENTION

The present invention relates to a new and distinct cultivar of New Guinea *Impatiens,* botanically known as *Impatiens hawkeri* and hereinafter referred to by the name 'Tamar White Improved'.

The new *Impatiens* is a product of a planned breeding program conducted by the Inventor in De Lier, The Netherlands. The objective of the breeding program is to create new freely-branching New Guinea *Impatiens* cultivars with freely flowering habit and large attractive flowers.

The new *Impatiens* originated from a cross-pollination made by the Inventor in 2000 in De Lier, The Netherlands of the *Impatiens hawkeri* cultivar Tamar White, disclosed in U.S. Plant Pat. No. 12,370, as the female, or seed, parent with the *Impatiens hawkeri* cultivar Harmony White, not patented, as the male, or pollen, parent. The new *Impatiens* was discovered and selected by the Inventor as a single flowering plant within the progeny of the stated cross-pollination in a controlled environment in De Lier, The Netherlands in 2001.

Asexual reproduction of the new *Impatiens* by terminal cuttings in a controlled environment in De Lier, The Netherlands since 2001, has shown that the unique features of this new *Impatiens* are stable and reproduced true to type in successive generations.

SUMMARY OF THE INVENTION

The cultivar Tamar White Improved has not been observed under all possible environmental conditions. The phenotype may vary somewhat with variations in environment and cultural practices such as temperature and light intensity, without, however, any variance in genotype.

The following traits have been repeatedly observed and are determined to be the unique characteristics of 'Tamar White Improved'. These characteristics in combination distinguish 'Tamar White Improved' as a new and distinct cultivar of *Impatiens:*

1. Upright and outwardly spreading growth habit; mounded plant form.
2. Freely branching habit.
3. Dark green-colored leaves.
4. Freely flowering habit.
5. Large white-colored flowers.
6. Good garden performance.

Plants of the new *Impatiens* can be compared to plants of the female parent, the cultivar Tamar White. Plants of the new *Impatiens* differ from plants of the cultivar Tamar White in the following characteristics:

1. Plants of the new *Impatiens* are more vigorous and larger than plants of the cultivar Tamar White.
2. Plants of the new *Impatiens* have larger flowers than plants of the cultivar Tamar White.

Plants of the new *Impatiens* can be compared to plants of the male parent, the cultivar Harmony White. Plants of the new *Impatiens* differ from plants of the cultivar Harmony White in the following characteristics:

1. Plants of the new *Impatiens* are more compact than plants of the cultivar Harmony White.
2. Plants of the new *Impatiens* have smaller flowers than plants of the cultivar Harmony White.

Plants of the new *Impatiens* can be compared to plants of the *Impatiens* cultivar Moorea, disclosed in U.S. Plant Pat. No. 9,147. In side-by-side comparisons conducted in De Lier, The Netherlands, plants of the new *Impatiens* differed from plants of the cultivar Moorea in the following characteristics:

1. Plants of the new *Impatiens* were more uniform than plants of the cultivar Moorea.
2. Plants of the new *Impatiens* had darker green-colored foliage than plants of the cultivar Moorea.
3. Plants of the new *Impatiens* had larger flowers than plants of the cultivar Moorea.

BRIEF DESCRIPTION OF THE PHOTOGRAPHS

The accompanying colored photographs illustrate the overall appearance of the new *Impatiens,* showing the colors as true as it is reasonably possible to obtain in colored reproductions of this type. Colors in the photographs may differ slightly from the color values cited in the detailed botanical description which accurately describe the colors of the new *Impatiens*.

The photograph on the first sheet comprises a top perspective view of a typical flowering plant of 'Tamar White Improved' grown in a container.

The photograph on the second sheet is a close-up view of typical flowers of 'Tamar White Improved'.

DETAILED BOTANICAL DESCRIPTION

The aforementioned photographs and following observations, measurements and values describe plants grown in De Lier, The Netherlands, in 12-cm containers and under commercial practice during the summer in a glass-covered greenhouse with day and night temperatures averaging 18° C. Rooted young plants had been growing for about ten weeks when the photographs and description were taken. In the following description, color references are made to The Royal Horticultural Society Colour Chart, 1995 Edition, except where general terms of ordinary dictionary significance are used.

Botanical classification: *Impatiens hawkeri* cultivar Tamar White Improved.

Parentage:

*Female, or seed, parent.*—*Impatiens hawkeri* cultivar Tamar White, disclosed in U.S. Plant Pat. No. 12,370.

*Male, or pollen, parent.*—*Impatiens hawkeri* cultivar Harmony White, not patented.

Propagation:

*Type.*—By terminal cuttings.

*Time to initiate roots, summer.*—About five to seven days at temperatures of 19° C. to 20° C.

*Time to initiate roots, winter.*—About six to eight days at temperatures of 19° C. to 20° C.

*Time to produce a rooted young plant, summer.*—About 14 to 19 days at temperatures of 19° C. to 20° C.

*Time to produce a rooted young plant, winter.*—About 14 to 21 days at temperatures of 19° C. to 20° C.

*Root description.*—Fine; white to brown in color.

*Rooting habit.*—Freely branching.

Plant description:

*Plant and growth habit.*—Upright and outwardly spreading growth habit; mounded plant form. Freely branching habit with about eight lateral branches; pinching is typically not required. Moderately vigorous growth habit.

*Plant height.*—About 23 cm.

*Plant diameter.*—About 39 cm.

Lateral branch description:

*Length.*—About 16 cm.

*Diameter.*—About 8 mm.

*Internode length.*—About 4 cm.

*Strength.*—Moderately strong.

*Aspect.*—Initially upright to outwardly spreading.

*Texture.*—Smooth, glabrous; slightly glossy in luster.

*Color.*—Between 146B and 146C.

Foliage description:

*Arrangement.*—Opposite or in whorls of about five; simple.

*Length.*—About 10 cm.

*Width.*—About 4 cm.

*Shape.*—Elliptic.

*Apex.*—Acute.

*Base.*—Attenuate.

*Margin.*—Serrate with ciliation.

*Texture, upper and lower surfaces.*—Smooth, glabrous; leathery; moderately glossy in luster.

*Venation pattern.*—Pinnate; arcuate.

*Color.*—Developing foliage, upper surface: 144A to 146A. Developing foliage, lower surface: 139C. Fully expanded foliage, upper surface: Darker than between 139A and 147A; venation, 194C. Fully expanded foliage, lower surface: 138B; venation, 194B and 138B.

*Petiole.*—Length: About 3 cm. Diameter: About 3 mm. Texture, upper and lower surfaces: Smooth, glabrous. Color, upper and lower surfaces: 145C.

Flower description:

*Flower type and flowering habit.*—Single rounded axillary flowers. Freely flowering habit; usually about twenty flowers develop per lateral branch. Flowers positioned above the foliage and typically face upright or outward. Flowers last about ten days under greenhouse conditions. Petals self-cleaning, gynoecium persistent. Flowers not fragrant.

*Natural flowering season.*—Year-round under greenhouse conditions. In the garden, flowering from spring until fall in The Netherlands. Plants begin flowering about nine weeks after planting.

*Flower size.*—Diameter: About 5 cm. Depth: About 1.8 cm.

*Flower buds.*—Length: About 1 cm. Diameter: About 8 mm. Shape: Ovoid; pointed. Color: Between 155D and 150D.

*Petals.*—Quantity/arrangement: Five per flower in a single whorl. Length, banner petal: About 1.8 cm. Length, lateral and lower petals: About 2.5 cm. Width, banner petal: About 3.5 cm. Width, lateral and lower petals: About 2.5 cm. Shape, banner petal: Roughly reniform. Shape, lateral and lower petals: Broadly cordate. Apex: Emarginate. Base: Acute. Margin: Entire. Texture, upper and lower surfaces: Smooth, glabrous. Color: When opening, upper and lower surfaces: Close to 155D. Fully opened, upper and lower surfaces: Close to 155D.

*Sepals.*—Quantity/arrangement: Three; one modified into an elongated spur. Length: About 1 cm. Width: About 6 mm. Shape: Ovate. Apex: Apiculate. Base: Cuneate. Margin: Entire. Texture, upper and lower surfaces: Smooth, glabrous. Color, upper and lower surfaces: 144B. Spur length: About 5 cm. Spur diameter: At flower, about 2 mm; at apex, less than 1 mm. Spur texture: Smooth, glabrous. Spur color, upper and lower surfaces: 145D.

*Peduncles.*—Length: About 5.1 cm. Diameter: About 2.1 mm. Angle: About 45° from vertical. Strength: Moderately strong. Texture: Smooth, glabrous. Color: 145A.

*Reproductive organs.*—Stamens: Quantity: Five fused at anthers; filaments free. Anther length: About 2 mm. Anther color: 182D. Pollen amount: Scarce. Pollen color: 158D. Pistils: Quantity per flower: One. Pistil length: About 1 mm. Stigma shape: Rounded. Stigma color: 155B. Ovary color: 143A.

*Seed/fruit.*—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate wind, rain and temperatures ranging from about 4° C. to about 35° C.

It is claimed:

1. A new and distinct *Impatiens* plant named 'Tamar White Improved' as illustrated and described.

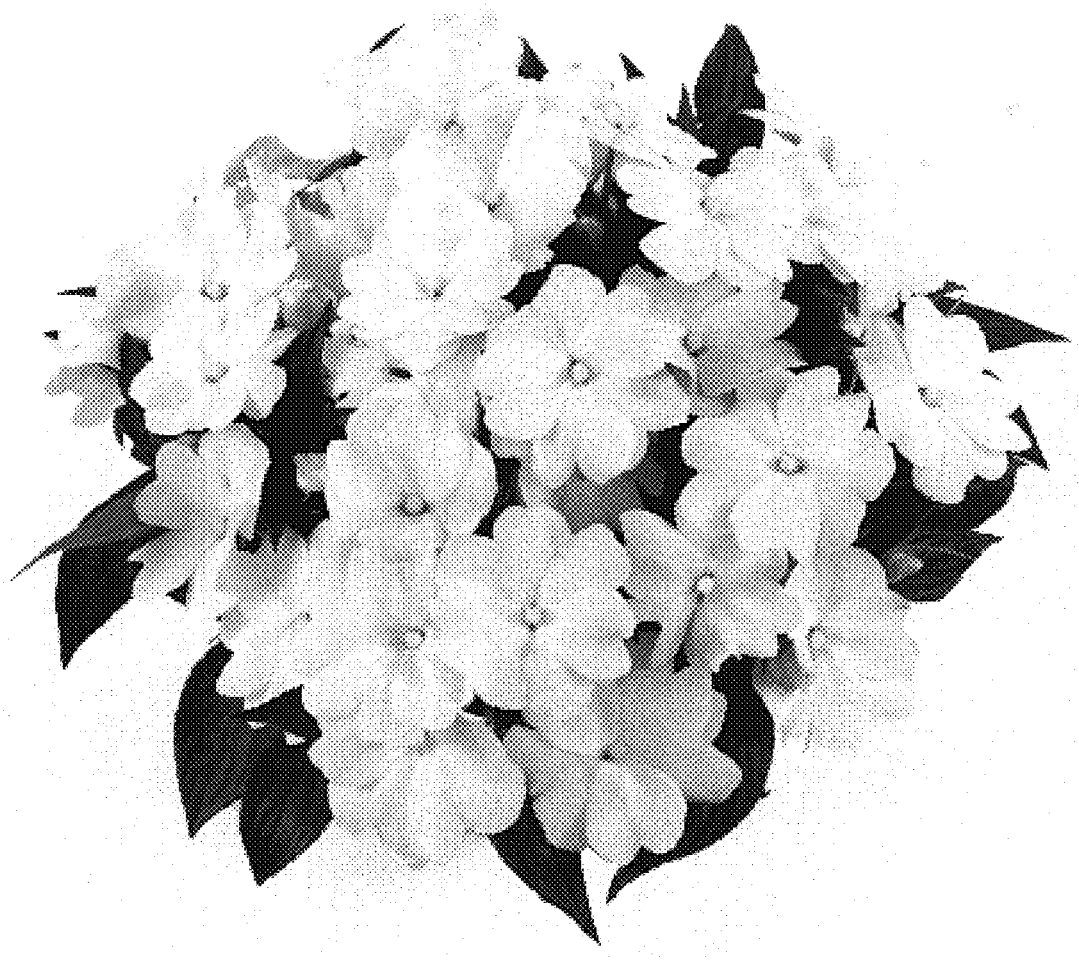

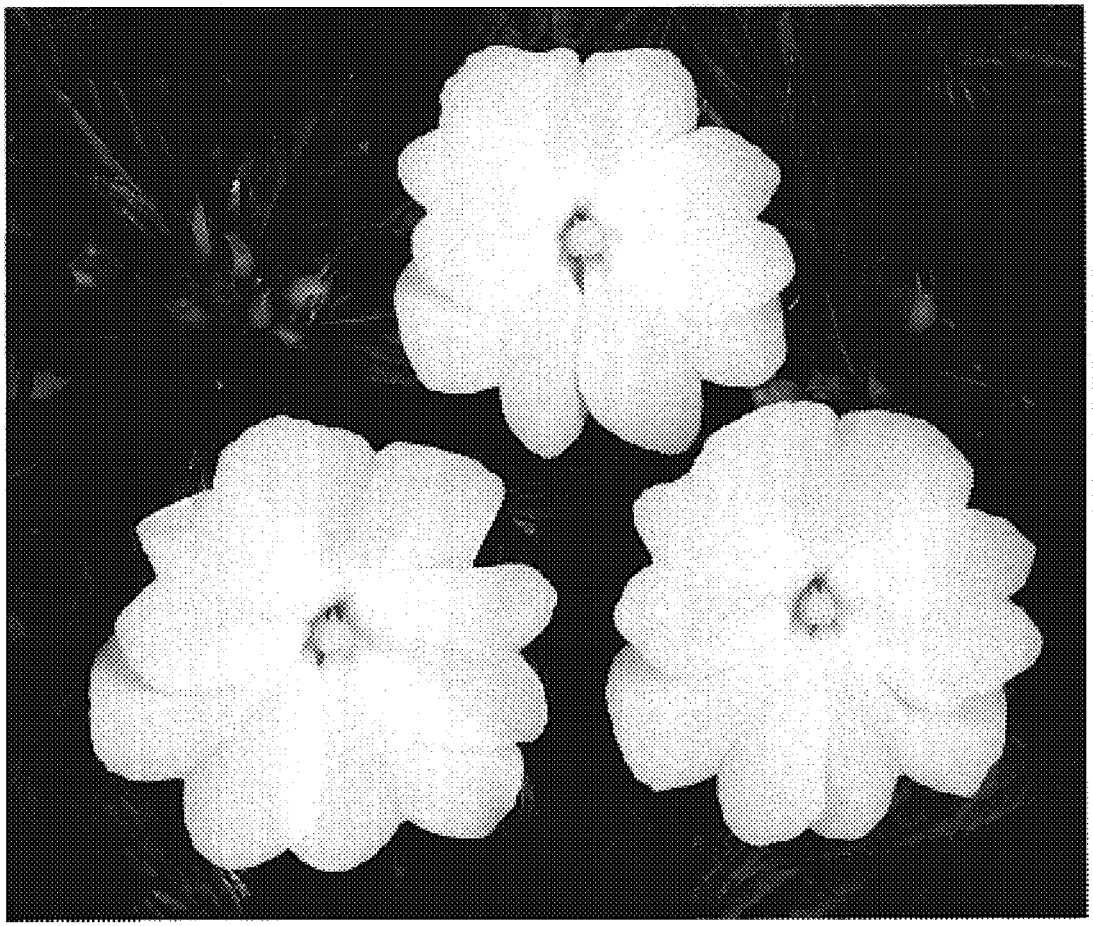

* * * * *